United States Patent
Yamakawa et al.

(10) Patent No.: US 7,344,866 B2
(45) Date of Patent: Mar. 18, 2008

(54) METHOD OF TESTING FOOD

(75) Inventors: Hirohito Yamakawa, Saitama (JP); Eriko Suzuki, Saitama (JP); Kiyoko Miyatake, Saitama (JP); Katsuyuki Hayakawa, Saitama (JP)

(73) Assignee: Nisshin Seifun Group Inc., Tokyo (JP)

( * ) Notice: Subject to any disclaimer, the term of this patent is extended or adjusted under 35 U.S.C. 154(b) by 159 days.

(21) Appl. No.: 10/504,589

(22) PCT Filed: Sep. 26, 2002

(86) PCT No.: PCT/JP02/09982

§ 371 (c)(1),
(2), (4) Date: Aug. 16, 2004

(87) PCT Pub. No.: WO03/068964

PCT Pub. Date: Aug. 21, 2003

(65) Prior Publication Data

US 2006/0057572 A1  Mar. 16, 2006

(30) Foreign Application Priority Data

Feb. 15, 2002  (JP) .............................. 2002-038930

(51) Int. Cl.
C12P 19/34 (2006.01)

(52) U.S. Cl. .................................................. 435/91.2

(58) Field of Classification Search ................ None
See application file for complete search history.

(56) References Cited

FOREIGN PATENT DOCUMENTS

JP  2001-309786  11/2001
WO  WO 98/04737  2/1998

OTHER PUBLICATIONS

Holzhauser et. al. (2000) Eur Food Res Technol 211: 360-365.*
Wieslander (1996) Allergy 51 (10) ;661-5.*
Park et. al. (2000) Allergy 55:1035-1041.*
Buck et al. (1999) Bio Techniques 27; 528-536.*
English translation of Futo, S. (Aug. 2002) Shokuhin Eiseigaku Zasshi (japanese) 43 (No. 4): J280-J282.*
Original Document by Futo, S. (Aug. 2002) Shokuhin Eiseigaku Zasshi (japanese) 43 (No. 4): J280-J282.*
GenBank Accession No. AF152003 search results us-10-504-589a-11.rge pp. 1-2, 1999 Nair et al Fagopyrum 16: 29-36.*
Nair et al., A molecular-genetic approach for hypoallergenic buckwheat. Fagopyrum, vol. 16,(1999) pp. 29 to 36.
Sukenobu Fujino, "Soba Allergy no Genin o Saguru, Allergen Protein wa Dokomade Kaimei Saretaka?" Kagaku to Seibutsu, Nov. 2001, vol. 39, No. 11, pp. 707 to 708.
Fujino et al., Expression, Cloning, and Immunological Analysis of Buckwheat (*Fagopyrum esculentum* Moench) Seed Storage Proteins. J. Agric. Food Chem., vol. 49, No. 4(2001) pp. 1825 to 1829.
Hsih et al., "Combination of Immunomagnetic Separation and Polymerase Chain Reaction for the Simultaneous Detection of *Listeria monocytogenes* and *Salmonella* spp. In Food Samples", Journal of Food Protection, vol. 64, No. 11, 2001, XP-001085205, pp. 1744-1750.
Meyer et al., "PCR-based DNA Analysis for the Identification and Characterization of Food Components", Lebensmittel Wissenschaft und Technologie, vol. 29, No. 1-2, 1996, XP-002225828, pp. 1-9.
Van der Vossen et al., "DNA based typing, identification and detection systems for food spoilage microorganisms: development and implementation", International Journal of Food Microbiology, vol. 33, No. 1, 1996, XP-002239603, pp. 35-49.
Allmann et al., "Polymerase chain reaction (PCR): a possible alternative to immunochemical methods assuring safety and quality of food—Detection of wheat contamination in non-wheat food products", Zeitschrift Fuer Lebensmitteluntersuchung und Forschung, vol. 196, No. 3, 1993, XP009014433, pp. 248-251.
Holzhauser et al, "Polymerase chain reaction (PCR) for detection of potentially allergenic hazelnut residues in complex food matrixes", Eur Food Res Technol, vol. 211, 2000, XP-002354383, pp. 360-365.
Nachr. Chem. Tech. Lab, 47, 1, 1999, XP009057277, pp. 30-32.
J. Szamos et al., "Detection of Wheat by Adapted Polymerase Chain Reaction (PCR) Methodology", Acta Alimentaria, vol. 27(1), pp. 87-95, 1998.

* cited by examiner

Primary Examiner—Gary Benzion
Assistant Examiner—Suchira Pande
(74) Attorney, Agent, or Firm—Young & Thompson

(57) ABSTRACT

A method for detecting the presence/absence of a specific substance in foods by performing PCR using primers which are designed on the basis of data obtained from a part of a gene of the specific substance. This method is highly useful in detecting a trace component contained in a food or identifying a specific harmful allergen.

9 Claims, 3 Drawing Sheets

SEQUENCE LISTING

<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: FAG3,
    designed sense primer based on SEQ ID NO: 11 between 149 and
    169

<400> SEQUENCE: 1
ccagcaattc cagcatcagt g                                           21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: FAG4,
    designed anti-sense primer based on SEQ ID NO: 11 between 334
    and 313

<400> SEQUENCE: 2
ttggagtagg aaggaagcaa ga                                          22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: FAG5,
    designed sense primer based on SEQ ID NO: 11 between 278 and
    297

-continued

```
<400> SEQUENCE: 3
tgtcgccgtc cgtgtcgtaa                                          20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: FAG6,
      designed anti-sense primer based on SEQ ID NO: 11 between 530
      and 510

<400> SEQUENCE: 4
ggattcttcg ctctcactct g                                        21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: FAG17,
      designed sense primer based on SEQ ID NO: 11 between 1435 and
      1455

<400> SEQUENCE: 5
tggagtgggt ggagttgaag a                                        21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: FAG18,
      designed anti-sense primer based on SEQ ID NO: 11 between 1624
      and 1604

<400> SEQUENCE: 6
tcatctcggg actggaatgg t                                        21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: FAG19,
      designed sense primer based on SEQ ID NO: 11 between 1464 and
      1484

<400> SEQUENCE: 7
aacgccataa ccagcccgat t                                        21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: FAG20,
      designed anti-sense primer based on SEQ ID NO: 11 between 1626
      and 1606

<400> SEQUENCE: 8
tctcatctcg ggactggaat g                                        21

<210> SEQ ID NO 9
<211> LENGTH: 20
<212> TYPE: DNA
```

```
<213> ORGANISM: Artificial Sequence
<220> FEATURE:
<223> OTHER INFORMATION: Description of Artificial Sequence: FAG22,
      designed anti-sense primer based on SEQ ID NO: 11 between 1590
      and 1571

<400> SEQUENCE: 9
cctcctgcct cccattcttc                                                  20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: FAG24,
      designed anti-sense primer based on SEQ ID NO: 11 between 1592
      and 1572

<400> SEQUENCE: 10
aacctcctgc ctcccattct t                                                21

<210> SEQ ID NO 11
<211> LENGTH: 1825
<212> TYPE: DNA
<213> ORGANISM: Fagopyrum esculentum

<400> SEQUENCE: 11
gatcaccacc tcgacaacac aacttcaaac attccaccat gtcaactaaa ctcatactct        60
ccttctcact gtgccttatg gtactaagct gctctgcgca gctattgcca tggcagaagg       120
gacaacgcag ccgccccac catggacacc agcaattcca gcatcagtgt gatatccaga       180
ggctcaccgc tctgagccc tctcgtagag tccggtccga ggccggagtt actgagattt       240
gggaccatga caccctgag ttccgatgtg ccggatttgt cgccgtccgt gtcgtaattc       300
agcctggagg cctcttgctt ccttcctact ccaacgcccc ttacatcacc tttgtcgagc       360
aagggagggg agtgcaggga gtggtcgtgc caggatgccc ggagacgttc cagtcagggt       420
cggaatttga gtaccctcgg tctcagagag accaacgctc caggcagagt gagagcggag       480
aatccagccg tggagaccaa cgctccaggc agagtgagag cgaagaatcc agccgtggag       540
accaacgctc caggcagagt gagagcgaag aattcagccg tggagaccag caccagaaga       600
ttttcaggat cagagacggc gacgtcatcc catctcccgc cggtgtcgtg cagtggaccc       660
acaacaacgg tgacaacgat ctcatcagta tcactcttta cgatgccaac agcttccaga       720
accagctcga tgagaacgtt aggaacttct tcctagctgg tcagagcaag cagagcaggg       780
aggaccgccg cagccagcga cagactaggg aggaaggcag tgaccgccaa tcccgtgaga       840
gccaagacga cgaagcactt ctcgaagcaa acatcttgag tggattcgag gacgagatcc       900
tccaagaaat cttccgaaat gttgaccagg agaccatcag caagctcaga ggtgagaacg       960
accagagagg attcatcgtc caggctcggg acctcaaact ccgggtccca gaggagtatg      1020
aagaagaact ccagagggaa agaggtgaca ggaaaagagg tggaagcggg aggagcaatg      1080
gattggagca agcgttctgc aacctgaaat tcaggcaaaa tgttaacagg ccttctcgcg      1140
ccgacgtctt caacccacgc gccggtcgta tcaacaccgt agacagcaac aatctcccga      1200
tcctcgaatt catccaactt agcgcccagc acgtcgtcct ctacaagaat gcgatcctcg      1260
gaccgagatg gaacttgaac gcgcacagcg cactgtacgt gacgagagga gaaggaagag      1320
tccaggttgt cggagatgaa ggaagaagtg tgttcgacga caacgtgcag cgaggacaga      1380
tccttgtggt cccacaggga ttcgcagtgg tgttgaaggc aggaagagaa ggactggagt      1440
```

```
gggtggagtt gaagaacgac gacaacgcca taaccagccc gattgccggg aagacttcgg    1500
tgttgagggc gatccctgtg gaggttcttg ccaactccta cgatatctcg acgaaggaag    1560
cgttcagatt gaagaatggg aggcaggagg ttgaggtctt ccgaccattc cagtcccgag    1620
atgagaagga gagggagcgt ttctccatag tttaagagag acaaagggtc tatcgtatgc    1680
aaaataaaac agaaggagaa ggataaggga gtcttgtcta tcgtttagct agtcaagtcc    1740
ctcttccact tctgggttat gttctatgtt tttactttag tgtcaataaa agagtgaatt    1800
ctcgaaaaaa aaaaaaaaaa aaaaa                                          1825
```

METHOD OF TESTING FOOD

TECHNICAL FIELD

The present invention relates to a food testing method, and more specifically to a method for detecting presence of a specified substance contained in a food in a trace amount over the entire distribution stage in order to indicate the presence/absence of an allergic substance in the food.

BACKGROUND ART

Recently, to prevent health hazard attributed to foods containing allergic substances, requests for information service by indication thereof have increased. The indication of foods containing allergic substances has been made obligatory with enforcement of amendments to the Statutes on the Food Sanitation Law in April, 2001. In particular, with respect to five items (specified raw materials) of eggs, milk, and wheat which cause allergy most often, and buckwheat and peanuts which cause serious symptoms, it has been made obligatory to perform proper indication over the entire distribution stage. There are individual differences as to what food people recognize as an allergen as the allergic substance. Thus, if a specified substance contained in the food is properly indicated even when the specified substance is contained in a trace amount, a person who ingests the food can know the presence/absence of the allergen contained in the food. However, it has been difficult to detect the presence/absence of a trace amount of a specified substance in a food having been heated or otherwise processed, by conventionally known methods for food analysis.

When a specified substance is used by a producer in his or her company, it is a matter of course that the specified substance can be indicated on processed foods. However, when a specified substance is used as an intermediate material of a final product, it is hard in some cases to confirm the presence/absence of the specified substance contained in a trace amount, particularly in a purchased intermediate material. Unintended inclusion may also actually occur.

For food manufacturers, it is important to precisely comprehend food additives such as processing aids and carry-over remaining in trace amounts or actual states of mutual contamination between manufacturing lines, and take proper measures as well as provide consumers with correct information based on the laws. Therefore, it has been desired to provide a technology of precisely analyzing allergic substances.

In Japan, buckwheat is a common food, but there are patients who exhibit an allergic response to the buckwheat. Many responses are of anaphylaxis type, and in the most serious case, the responses result in death. In the indication of foods containing allergic substances under the Food Sanitation Law, the buckwheat has been defined as one of the specified raw materials, and it has been made obligatory to indicate the presence of the buckwheat when the buckwheat is included in the food. But, there has been no appropriate method for measuring the amount of buckwheat. Therefore, a reliable method for measuring a trace amount component has been desired.

Thus, it is an object of the invention to provide a method for measuring the presence/absence of a specified substance in a food based on the findings obtained from attempts to construct primers specific to buckwheat, to identify the detection limit thereof, and to apply the primers to processed foods for the purpose of developing a method for precisely analyzing the presence/absence of the buckwheat included in the food.

DISCLOSURE OF THE INVENTION

[1] The present invention relates to a method for measuring presence/absence of a specified substance in a food, including: designing primers based on genetic information obtained from a part of genes of the specified substance; and performing PCR.

[2] Further, the present invention relates to a method for measuring presence/absence of a specified substance for indicating the presence/absence of a trace amount component in the food, including: designing primers based on information obtained from a part of genes of the specified substance; and performing PCR.

[3] The present invention also relates to a method for measuring presence/absence of a specified substance in a food, including: designing primers based on information obtained from a part of genes of the specified substance; and performing PCR to discriminate the food containing an allergen of the specified substance harmful for food ingesting person, a method for providing information as to whether the food contains a specified substance containing an allergen harmful for patients with food allergy or suspects thereof, or a method for indicating one of these about a food. The foods include not only foods for human beings but also foods (feedstuff) for animals.

[4] Here, the specified substance includes preferably specified cereals.

[5, 6] In addition, the food may be a processed food or a food raw material.

[7] The present invention provides the method in which the specified cereals include buckwheat.

[8] Here, it is preferable that the gene be a buckwheat gene shown in SEQ ID NO:11, and the primers be:

(1) a sense primer and an anti-sense primer composed of at least 5 to 35 consecutive DNA fragments selected from information of a sequence from position 121 to position 360; or (2) a sense primer and an anti-sense primer composed of at least 5 to 35 consecutive DNA fragments selected from information of a sequence from position 1,381 to position 1,680.

The primers are complementary chains of a target gene, and sequence portions of N-terminus and C-terminus of the target gene are selected as a pair. Lengths in the pair may be the same or different.

[9] In particular, primer pairs of FAG 3 (SEQ ID NO:1)/ FAG 4 (SEQ ID NO:2), FAG 17 (SEQ ID NO:5)/FAG 18 (SEQ ID NO:6), FAG 19 (SEQ ID NO:7)/FAG 20 (SEQ ID NO:8), FAG 19 (SEQ ID NO:7)/FAG 22 (SEQ ID NO:9), and FAG 19 (SEQ ID NO:7)/FAG 24 (SEQ ID NO:10) shown in Table 1 are preferable.

It is known that if PCR primers used for PCR are used for amplifying substantially in the same region of template DNA (in the case of buckwheat, the sequence of SEQ ID NO:11 is illustrated), they have the same function and produce the same result (PCR product). In the case of wheat, for example the individual primer sequence has the same function even if it is shifted to several to over 10 nucleotides on the corresponding same template DNA sequence toward 5'-upstream side or 3'-downstream side.

Therefore, the preferable primer pairs are not limited to those in Table 1, and those which can substantially accomplish the same functions as those of the above primer pairs in Table 1 are also included in the preferable primer pairs.

For the above primers, the primer where one or several nucleotides are deleted, substituted, added, and/or inserted and which hybridizes to the corresponding region of the template DNA is substantially the same as the above primers. The preferable primers in the present invention for example, include the primers having sequence shifted by one to several nucleotides or over 10 nucleotides toward 5'-upstream/downstream side and/or 3'-upstream/downstream side on the corresponding template DNA sequence complementary to the sequence of the primers of SEQ ID NOS:1 to 10. The preferable primers also include at least 80%, more preferably 90% or more, and still more preferably 95% or more of consecutive sequence in SEQ ID NOS:1 to 10.

[10] Further, there is provided the method, in which a clear amplified band is given in Polygonaceae Fagopyrum analytes including tatary buckwheat (Fagopyrum tataricum) and/or buckwheat (Fagopyrum esculentum) (not including wild buckwheat) but is not given in analytes including Polygonaceae analytes excluding Fagopyrum (tatary buckwheat and/or buckwheat) but including wild buckwheat (Fallopia), and animal and plant materials (including food raw materials derived therefrom) except buckwheat on an electrophoresis of the analyte subjected to a gene amplification reaction using the primers.

[11] There are provided PCR primers which are designed based on information obtained from a part of genes of a specified substance, and a set of reagents (kit) containing the same for measuring presence/absence and/or a concentration of the specified substance in a food.

BRIEF DESCRIPTION OF THE DRAWINGS

FIG. 2 is an electrophorogram showing detection limit of a buckwheat detection system using PCR.

BEST MODE FOR CARRYING OUT THE INVENTION

Figure 1A:
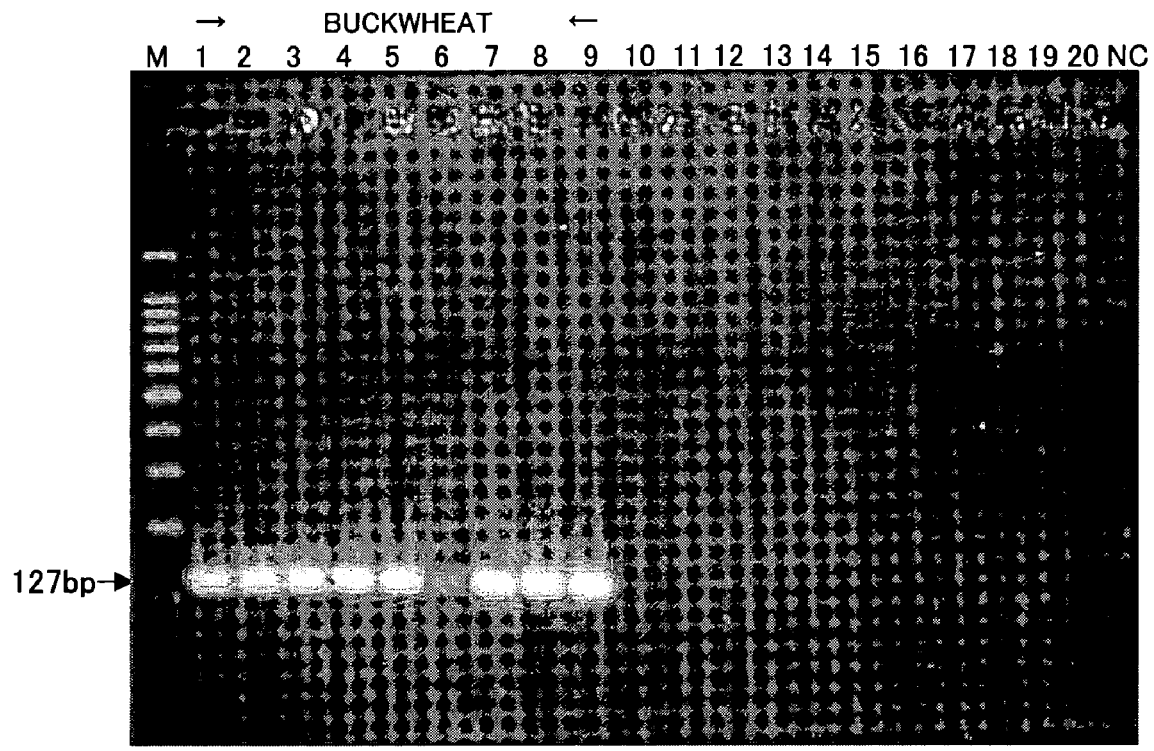
FIG. 1a is an electrophorogram (electrophoretic pattern) showing the specificity of buckwheat detection primers; FAG 19/22 to buckwheat.

The invention is more specifically illustrated.

The invention is a method for measuring the presence/absence of a specified substance in foods, comprising designing primers based on information obtained from a part of a gene of the specified substance and performing PCR.

The foods measured as subjects may be raw materials, materials in any step of processing, or foods after the processing. The method of the invention can detect the presence/absence of a specified substance or DNA thereof in a trace amount of preferably 0.1% or less, 100 ppm or less, further 50 ppm or less, and 10 ppm or less by weight ratio in food. With this method, if a gene of a specified substance is contained in a food, the presence/absence of the specified substance can be detected even when a substance which is not intended by a producer is present in a trace amount as a part of seasoning or an additive. DNAs are relatively stable by food processing such as heating compared to other substances derived from organisms such as proteins, and the presence in a trace amount can be detected in a food heated, cooked or otherwise processed.

A nucleotide sequence of the gene of the specified substance may be determined by any known methods when the sequence is unknown, but nowadays numerous known gene information can be used. For example, the information of the whole gene sequence of the specified substance is obtained from the database at National Institute of Genetics (DDBJ) and the like, and a pair (set) of a sense primer and an anti-sense primer suitable for PCR (Polymerase chain reaction) can be selected and designed based on the information on a part of the sequence to obtain the primers (probes).

In the design of the primers, attention was paid to the following items considering the testing method of the invention. (i) A GC content in a primer is from 40 to 60%; (2) A melting temperature (Tm value, see below) of a primer is from 55° C. to 70° C.; (iii) Tm values of two primers in the pair are close to each other; (iv) Two primers have no complementary sequences at 3' terminus; (v) The primer itself forms no high order structure such as hairpin; (vi) A full length of the primer is 15- to 35-mers; (vii) A GC content at 3' terminus of the primer is reduced; (viii) A sequence where the same nucleotide is consecutive in large numbers in the primer is avoided; (ix) The sequence of the primer is not necessary to be completely complementarily identical to that of the template DNA but complementarity at 3' terminus is increased; (x) There is no sequence complementarily identical to that of the primer in a DNA sample used.

The primers of the invention are required to be usable for not only buckwheat as a raw material but also foods during and after the processing such as heating and cooking. Further, it is considered that the template DNA of buckwheat is not intact but is fragmented. (xi) A region of the gene amplified by the two primers is a relatively short region. Moreover, it is necessary to design primers which fulfill all of the conditions of (i) to (xi) in one region of a gene that is commonly conserved in various species of buckwheat. However, it is very difficult to prepare primers which fulfill all of those conditions from DNA sequence composed of only four nucleotides, A, C, G, and T. Therefore, the design of the primers is a quite difficult problem when PCR is performed. Also, even if the primer that fulfills those many conditions can be designed, that is only a necessary condition for performing PCR. It is unknown whether the intended PCR is successful unless the PCR is actually performed.

A PCR method is not particularly limited and includes various known improved methods. In one example, a pair of primers and a template (analyte) DNA are mixed with reagents such as Tris-HCl, KCl, MgCl2, dNTPs, and Taq DNA polymerase to give a reaction solution for the PCR. One cycle of the PCR is composed of three steps: heat denaturation, annealing of the primers, and a DNA synthetic reaction by DNA polymerase. The respective steps require different or, in some cases the same reaction temperatures and times, and thus, proper ranges are determined depending on the nucleotide sequence and length of the DNA region to be amplified. A thermal cycler is commercially available for such manipulations. The following formula obtained from the GC content and the length of the sequence:

$$Tm\ (°\ C.) = 4 \times (G+C) + 2 \times (A+T)$$

is an indicator of the annealing temperature. The size of PCR product is adjusted to 50-500 bp, preferably about 100-150 bp. Within this range, DNA fragmented in the processed food can be detected.

When specified cereals include buckwheat, the above gene is a buckwheat gene shown in SEQ ID NO:11. The above primer is preferably (1) a sense or anti-sense primer which is composed of at least 5 to 35 consecutive DNA fragments selected from the sequence from position 121 to position 360 shown in SEQ ID NO:11; or (2) a sense or anti-sense primer which is composed of at least 5 to 35 consecutive DNA fragments selected from the sequence from position 1,381 to position 1,680. The primers are complementary chains of the target gene, and portions of N-terminus and C-terminus of the target gene are selected. Each length in the pair may be the same or different.

In particular, primer pairs of FAG 3 (SEQ ID NO:1)/FAG 4 (SEQ ID NO:2), FAG 17 (SEQ ID NO:5)/FAG 18 (SEQ ID NO:6), FAG 19 (SEQ ID NO:7)/FAG 20 (SEQ ID NO:8), FAG 19 (SEQ ID NO:7)/FAG 22 (SEQ ID NO:9), and FAG 19 (SEQ ID NO:7)/FAG 24 (SEQ ID NO:10) in Table 1 below or primer pairs which are substantially identical thereto are preferable. As described later in comparative example, even the primer pair of FAG 5 (SEQ ID NO:3)/FAG 6 (SEQ ID NO:4) which have the same Tm value is often unsuitable for the detection, and thus the selection of primers is important.

trophoresis apparatus. The reagents include dNTPs, MgCl2, Taq polymerase, Tris-HCl, glycerol, DMSO, DNA for positive control, DNA for negative control, and distilled water. Those reagents in the kit may be provided in an individually packed state or in a form where two or more reagents are mixed with each other. Concentrations of respective reagents in the kit are not particularly limited, and may be in the ranges suitable for the PCR of the invention. Also, the kit may include information on suitable PCR conditions or the like, or may be only composed of the primer reagents.

In the method of the invention, the substances to be detected are not limited so long as they are foods. To take cereals as an example, the test substances include wheat, rice, maize, foxtail millet, millet, Japanese millet, buckwheat, and beans. DNAs are stable to heat and can be detected in trace amounts in processed foods. Therefore, the obtained result can be utilized for indication on foods or as information on food allergies. In addition, by detecting the specified cereals in the food, it is possible to detect a trace amount of a specified substance remaining in food additives such as processing aids and carry-over or inclusion which is not intended by a producer such as mutual contamination between manufacturing lines.

Hereinafter, the present invention is concretely illustrated using buckwheat as an example, but the invention is not limited thereto.

TABLE 1

| Name | SEQ ID NO | Sequence | Tm | GC % | Primer setting position START | END |
|---|---|---|---|---|---|---|
| sense FAG 3 | 1 | 5' CCA GCA ATT CCA GCA TCA GTG 3' | 64 | 52 | 149 | 169 |
| anti-sense FAG 4 | 2 | 5' TTG GAG TAG GAA GGA AGC AAG A 3' | 64 | 45 | 334 | 313 |
| sense FAG 5 | 3 | 5' TGT CGC CGT CCG TGT CGT AA 3' | 64 | 60 | 278 | 297 |
| anti-sense FAG 6 | 4 | 5' GGA TTC TTC GCT CTC ACT CTG 3' | 64 | 52 | 530 | 510 |
| sense FAG 17 | 5 | 5' TGG AGT GGG TGG AGT TGA AGA 3' | 64 | 52 | 1,435 | 1,455 |
| anti-sense FAG 18 | 6 | 5' TCA TCT CGG GAC TGG AAT GGT 3' | 64 | 52 | 1,624 | 1,604 |
| sense FAG 19 | 7 | 5' AAC GCC ATA ACC AGC CCG ATT 3' | 64 | 52 | 1,464 | 1,484 |
| anti-sense FAG 20 | 8 | 5' TCT CAT CTC GGG ACT GGA AGT 3' | 64 | 52 | 1,626 | 1,606 |
| sense FAG 19 | 7 | 5' AAC GCC ATA ACC AGC CCG ATT 3' | 64 | 52 | 1,464 | 1,484 |
| anti-sense FAG 22 | 9 | 5' CCT CCT GCC TCC CAT TCT TC 3' | 64 | 60 | 1,590 | 1,571 |
| sense FAG 19 | 7 | 5' AAC GCC ATA ACC AGC CCG ATT 3' | 64 | 52 | 1,464 | 1,484 |
| anti-sense FAG 24 | 10 | 5' AAC CTC CTG CCT CCC ATT CTT 3' | 64 | 52 | 1,592 | 1,572 |

When suitable PCR conditions such as concentrations of Taq DNA polymerase and MgCl2, and the reaction cycle number are examined or nested PCR is used, there is a possibility that detection sensitivity is further increased.

A PCR product may be identified using an immune reaction or by any other method. When a clear band is observed on an electrophorogram obtained by performing electrophoresis using positive and negative controls if necessary, the presence of a test substance in an analyte can be confirmed.

The method of the invention can be easily conducted by using a set of reagents (kit) containing the primers designed based on the information obtained from a part of the gene of the specified substance. The set of the reagents (kit) may contain known reagents conventionally used for PCR, or may be equipped with another apparatus such as an elec- (1) Construction of Primers for Detection of Buckwheat Before constructing primers for the detection of DNA derived from buckwheat, the inventors accessed the database in the National Institute of Genetics (DDBJ), searched for known genes of buckwheat (Fagopyrum esculentum), and selected Fagopyrum esculentum major allergenic storage protein gene (Accession #AF152003, full length: 1,825 bps) from genetic information concerning buckwheat. Next, it was confirmed by the BLAST search in DDBJ that there is no similar sequence to the sequence of the selected buckwheat gene in plants other than the buckwheat.

In order to design the primer, the inventors searched for sequences which are candidates of the primers for a gene sequence of a specified substance using software "GENE-TYX MAC". GENETYX MAC used can set up various conditions for primer design, e.g., (i) GC content and (ii)

range of Tm value which were difficult to determine by manual calculation. As a result, 67 pairs of the candidate primers were found. The inventors have uniquely searched for the sequences which fulfill all of the above conditions (i) to (xi) for the primer design and found primer sequences usable in the testing method of the invention. Nine pairs of oligonucleotide primers (synthesized by Biologica Co.) including the thus found primer sequences were prepared.

(2) Extraction of DNA

Surfaces of seeds of buckwheat and other plants were washed with 1% Triton X (Wako Pure Chemical Industries Ltd.), rinsed with distilled water, dried well, and then the seeds were finely ground with Multi Bead Shocker (Yasui Kikai Co., Ltd.). Next, DNA was extracted from 1 to 1.5 g of a ground sample using Dneasy Plant Maxi kit (Qiagen). For processed foods, those whose water content was high were lyophilized for 24 hours, and those whose water content was low were directly used. Then, DNA was extracted from 1 g of each by using Genomic Tip 20/G (Qiagen). The concentration of the extracted DNA was determined by measuring the absorbance, and subsequently the DNA was diluted with purified water to 10 ng/μl and was used as a template (test) DNA sample of PCR.

(3) Detection of Buckwheat by PCR and Electrophorogram

A reaction solution of PCR was prepared as follows. 2.5 μl of a DNA sample solution adjusted to 10 ng/μl was added to a solution containing PCR buffer (PCR buffer II, Applied Biosystems), 200 μmol/L of dNTP, 1.5 mmol/L of MgCl2, 0.5 μmol/L of sense and anti-sense primers, and 0.625 unit of Taq DNA polymerase (AmpliTaq, Gold, Applied Biosystems) to obtain a total volume of 25 μl. Those with no description of a template DNA amount in Table 3 have this concentration. But, when the concentration of the extracted DNA was 10 ng/μl or less, when the absorbance OD260/OD280 of the DNA obtained from processed foods or the like containing many additives was 1.7 or less, the DNA was containing many impurities. When the purity of the DNA was low, 2.5 μl to 17.8 μl of the undiluted DNA solution or 10 ng/μl diluted solution was added to the PCR reaction solution, and the total volume was adjusted to 25 μl with purified water. Those with the description of the template DNA amount in Table 3 have this concentration.

GeneAmp PCR System 9600 (Applied Biosystems) was used as a PCR amplification apparatus, and reaction conditions were set as follows. First, the temperature was retained at 95° C. for 10 min, and the reaction was started. Next, 95° C. for 30 sec, 60° C. for 30 sec, and 72° C. for 30 sec were set as one cycle, and 40 cycles of PCR were performed. Finally, a termination reaction at 72° C. for 7 min was conducted, and subsequently the solution was stored at 4° C. to give a PCR product solution.

The PCR product solution was subjected to electrophoresis using 2% agarose gel (2% E-Gel, Invitrogen) containing ethidium bromide. Validity of the PCR was determined by the presence/absence of an amplified band from a positive control (DNA extracted from the buckwheat flour) and a negative control (blank reaction solution without template DNA). Then, the presence/absence of buckwheat in the sample was determined by identifying a DNA amplified band with optimal size produced by each set of primers.

(4) Experiment 1. Confirmation of Specificity of Primers for Buckwheat Detection For the purpose of selecting primers for specific detection of the buckwheat, PCR was performed using DNAs extracted from seeds of buckwheat and other plants. As samples of the buckwheat, 7 species of buckwheat seeds [Mancan (U.S., Canada, China), Nei Mongol (China), Yurin (China), Kitawase (Hokkaido), Aizu Domestic (Fukushima)] and two species of buckwheat flours A and B for business use were used. Also, the seeds of two species of wheat (Norin 61, Canadian Amber Durum), rye (Canada), barley (Minorimugi), rice (Koshihikari), maize (non GMO for feedstuff), soybean (Murayutaka), foxtail millet (Kumamoto), rapeseed (Canola), oat or oats (feedstuff for racehorse) and wild buckwheat (obtained from Research Institute for Bioresources, Okayama University) were used as the other plants.

After the PCR, electrophoresis was performed, and primers which afforded a clear amplified band with optimal size only in the buckwheat samples but not in the other samples were selected as the primers which can specifically detect the buckwheat.

FIG. 1a is an electrophorogram showing the specificity of the primers for buckwheat detection; FAG 19/22. In FIG. 1a, M represents 100 bp ladder marker and NC represents no template control (blank without template DNA). Table 2 below shows lane numbers (sample names) in FIG. 1a and the results thereof.

Figure 1B:
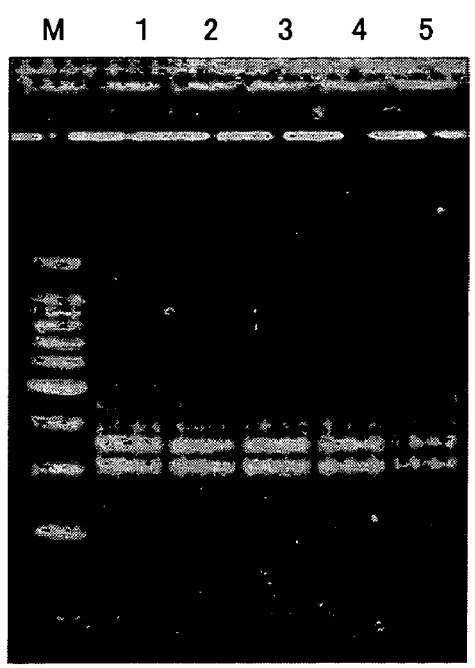
FIG. 1b shows the specificity of FAG 5/FAG 6.

FIG. 1b is an electrophorogram showing the specificity of the primers: FAG 5/FAG 6 shown in Table 1. In FIG. 1b, a lane number 1: Mancan species (Canada), 2: Nei Mongol species (China), 3: Yurin species (China), 4: Aizu domestic species (Japan), 5: buckwheat flour A for business use, and M: 100 bp ladder marker. In FIG. 1b, non-specific bands appeared, which shows that the primers are not suitable as the primers for buckwheat detection.

TABLE 2

Specificity of primers for buckwheat detection; FAG 19/22

| Sample name | Cultivar | Production area | Detection result by PCR | Lane number in FIG. 1 |
|---|---|---|---|---|
| Buckwheat seeds | Mancan | US | + | 1 |
| Buckwheat seeds | Mancan | Canada | + | 2 |
| Buckwheat seeds | Mancan | China | + | 3 |
| Buckwheat seeds | Nei Mongol | China | + | 4 |
| Buckwheat seeds | Yurin | China | + | 5 |
| Buckwheat seeds | Kitawase | Hokkaido | + | 6 |
| Buckwheat seeds | Aizu domestic | Fukushima | + | 7 |
| Buckwheat flour A | | | + | 8 |
| Buckwheat flour B | | | + | 9 |
| Wheat | Norin 61 | Japan | − | 10 |

TABLE 2-continued

Specificity of primers for buckwheat detection; FAG 19/22

| Sample name | Cultivar | Production area | Detection result by PCR | Lane number in FIG. 1 |
|---|---|---|---|---|
| Wheat (Durum) | CAD (Canadian Amber Durum) | Canada | – | 11 |
| Rye | | Canada | – | 12 |
| Barley | Minorimugi | Japan | – | 13 |
| Rice | Koshihikari | Japan | – | 14 |
| Maize | nonGMO (feedstuff) | Australia | – | 15 |
| Soybean | Murayutaka | Japan | – | 16 |
| Foxtail millet | Kumamoto | Japan | – | 17 |
| Rapeseed | Canola | Canada | – | 18 |
| Oat | Feedstuff for racehorse | Canada | – | 19 |
| Wild buckwheat | Obtained from Research Institute for Bioresources, Okayama University | Japan | – | 20 |

As a result of the experiment 1, a set of FAG19/22 (amplified size: 127 bps) was selected as the primers in the following experiment.

FAG 19 (sense primer): 5'-AAC GCC ATA ACC AGC CCG ATT-3'

FAG 22 (anti-sense primer): 5'-CCT CCT GCC TCC CAT TCT TC-3'

Among the plants except the buckwheat, the wild buckwheat belongs to the same Polygonaceae family as the buckwheat, but this primer set exhibited no cross reaction in the wild buckwheat sample (FIG. 1a, Table 2).

(5) Experiment 2. Identification of Detection Limit of Buckwheat by PCR

In the experiment 2, for the purpose of examining the detection limit of buckwheat by PCR using FAG 19/22 primers, artificially mixed samples of buckwheat were prepared at DNA level and powder level, and PCR was performed using solutions of the samples to identify the detection limit of buckwheat.

The artificially mixed samples at the DNA level were prepared by: diluting DNAs extracted from the seeds of wheat and buckwheat to 10 ng/µl, respectively; and mixing wheat DNA and buckwheat DNA so that the ratios of the buckwheat DNA to the wheat DNA were 0.1 ppm, 10 ppm, 50 ppm, 100 ppm, 1,000 ppm and 1% by volume. Alternatively, the artificially mixed samples at the powder level were prepared by mixing wheat flour and buckwheat flour so that the mixed ratios of buckwheat flour to wheat flour were 0.1 ppm, 10 ppm, 50 ppm, 100 ppm, 1,000 ppm, and 1% by weight. Subsequently, each mixed sample was finely ground, and then DNA was extracted.

Figure 2A:
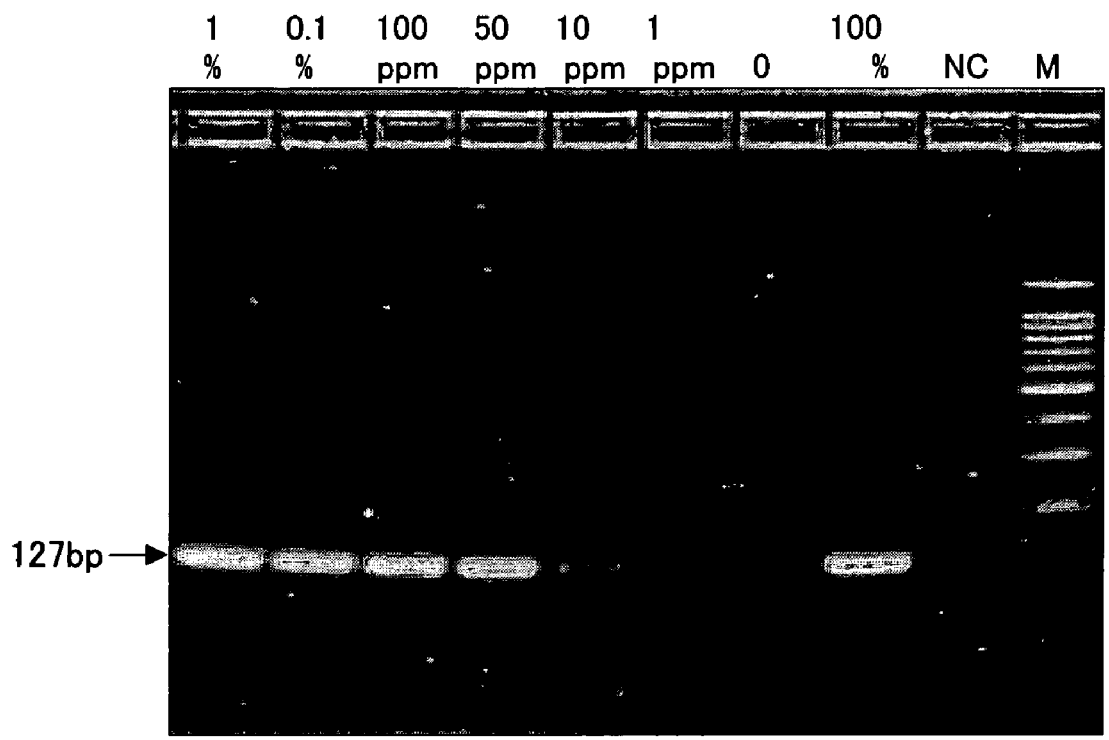
FIG. 2a shows measurement of artificially mixed samples of DNA level.
Figure 2B:
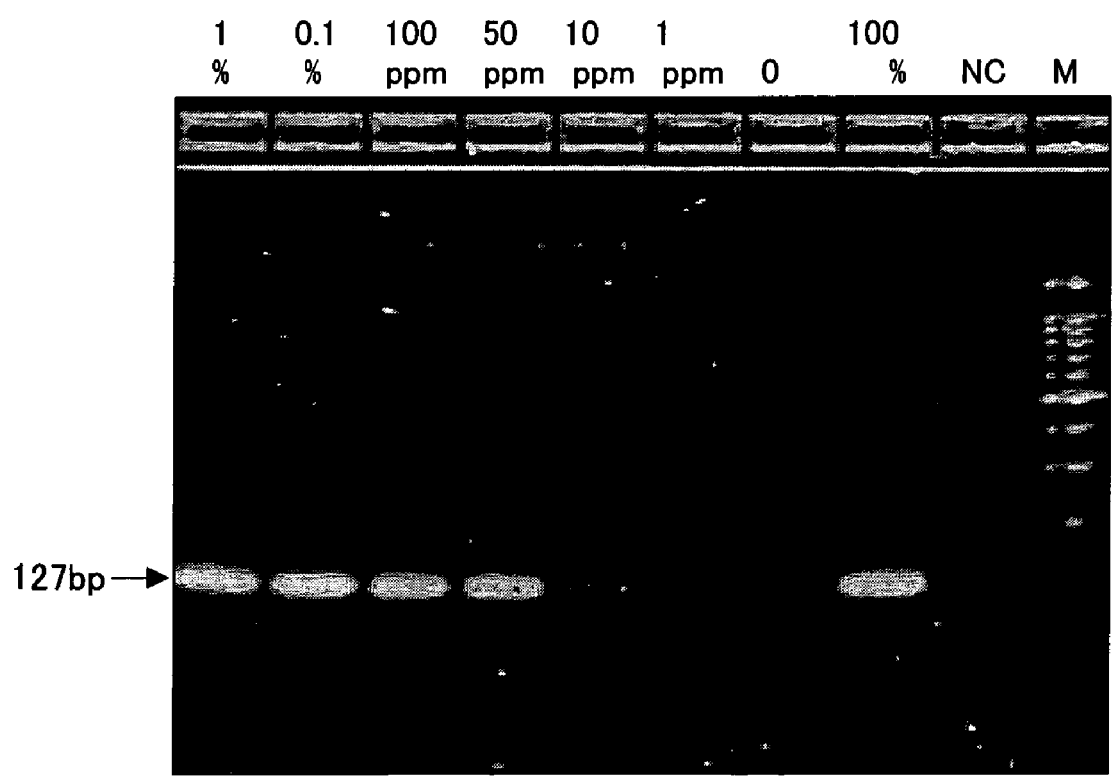
FIG. 2b is an electrophorogram showing measurement of artificially mixed samples of powder level.

FIGS. 2a and 2b are electrophorograms showing results of the detection. Upper numerals indicate the content of buckwheat, and M represents 100 bp ladder and NC represents no template control (blank without template DNA). In FIG. 2a, the samples at the DNA level prepared by diluting the buckwheat DNA with the wheat DNA were used for the analyte. In FIG. 2b, the samples at the powder level prepared by diluting the buckwheat flour with the wheat flour were used for the analyte.

In the experiment 2, the detection limit of buckwheat by PCR using FAG 19/22 was identified. Results show that the detection limit of buckwheat in both the samples at the DNA and powder levels was 10 ppm (FIG. 2). In the experiments repeated multiple times, however, the detection limit was 50 ppm in several experiments, and thus, it has been suggested that the limit stably detectable by this PCR is 50 ppm. A food allergy sometimes occurs in certain people by a trace amount of an allergic substance. Therefore, the food containing a designated raw material must be indicated even in a trace amount regardless of its amount according to "obligation to indicate the foods containing allergic substances" with the enforcement of amendments of the Food Sanitation Law. Criteria by which necessity of the indication is determined are given in the interim report (Oct. 17, 2001) in the Conference on Allergy Indication in the Ministry of Health, Labour and Welfare, and it is reported that the indication is necessary when a specified raw material is contained in a processed food in an amount of several µg/ml (g) or more (1 to 9 ppm or more) in terms of total protein amount. The protein content in whole buckwheat flour is about 12% by weight (according to the Food Composition Table, 5th edition), and thus, 50 ppm of the detection limit by the PCR corresponds to 6 ppm of the mixing ratio of the buckwheat protein. Accordingly, it is expected that the method for detecting the buckwheat by the PCR as mentioned above is an analytical method sufficiently suitable to detect the indication criteria presented by the Conference on Indication.

(6) Experiment 3. Detection of Buckwheat in Processed Foods by PCR

The detection of buckwheat was performed from processed foods containing buckwheat as a raw material using FAG 19/22 as the primers. Samples used were two kinds of dried noodles (100 percent buckwheat noodle, 30 percent buckwheat noodle), four kinds of confectionery (buckwheat cakes A and B, fried buckwheat dough cake, buckwheat cookie, baked goods), and buckwheat tea. The samples were each finely ground. Subsequently, DNAs were extracted from the dried noodles using Dneasy Plant Maxi kit (Qiagen), and from the confectionery and the tea using Genomic Tip 20/G (Qiagen) and the extracted DNAs were subjected to the PCR. Since the DNA purity obtained from the buckwheat cake B was as low as 1.2, 50 to 1,800 ng of the DNA (as calculated from the absorbance) per tube was used for the PCR reaction.

Figure 3A:
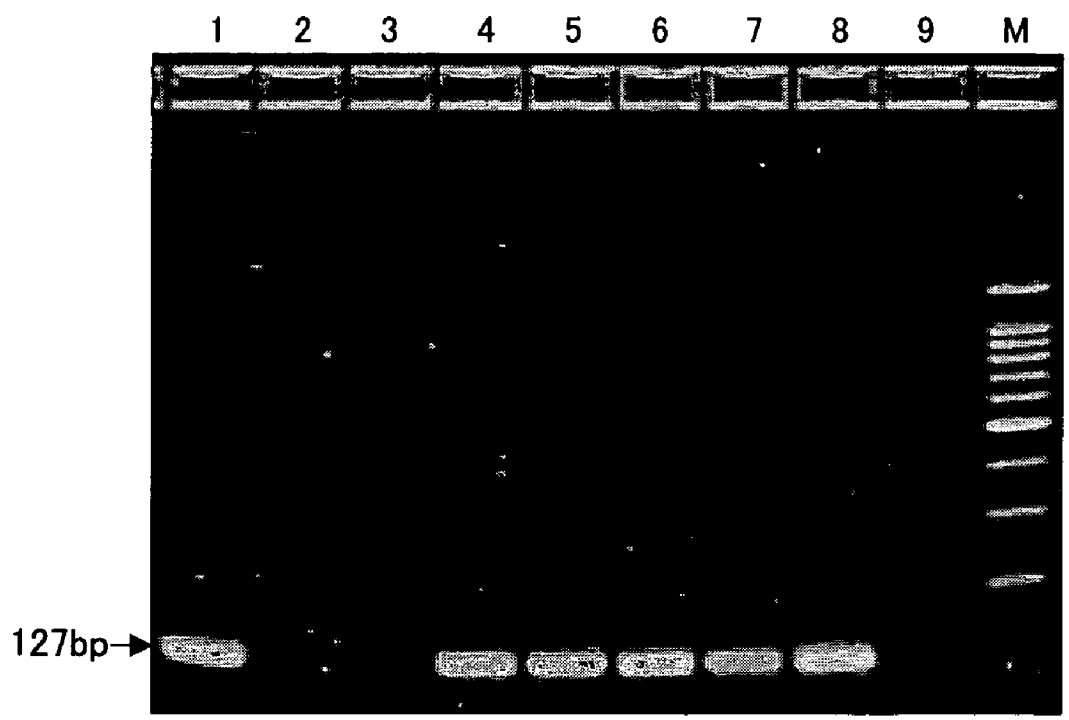
FIG. 3 is an electrophorogram showing results of detection of buckwheat in processed foods by PCR. The kinds of the processed foods measured in FIGS. 3a and 3b are different from one lane to another.
Figure 3B:
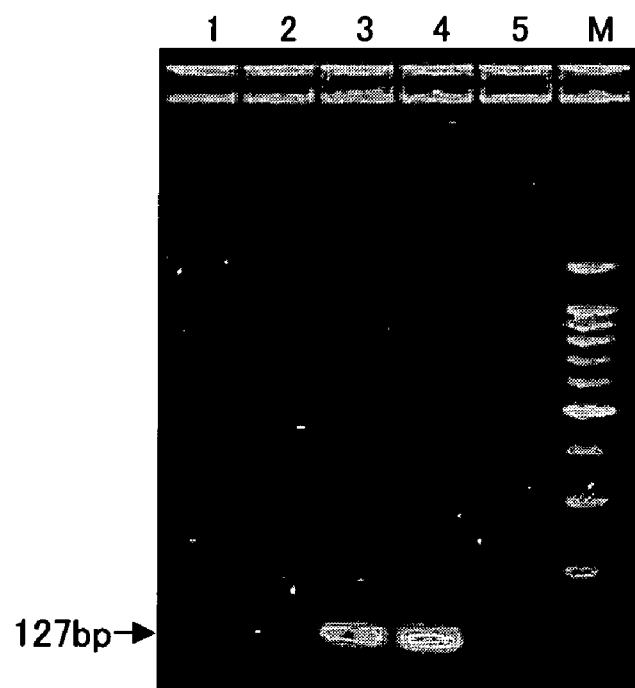

Table 3 shows lane numbers (sample names) in FIGS. 3a and 3b.

Table 3

TABLE 3

| Lane number | | Sample name |
|---|---|---|
| FIG. 3a | 1 | Buckwheat cake A |
| | 2 | Buckwheat cake B |
| | | (template DNA amount: 50 ng/tube) |
| | 3 | Buckwheat cake B |
| | | (template DNA amount: 120 ng/tube) |
| | 4 | Fried buckwheat dough cake |
| | 5 | Buckwheat cookie |
| | 6 | Baked buckwheat goods |
| | 7 | Buckwheat tea |
| | 8 | Buckwheat seeds |
| | 9 | Water |
| | M | 100 bp ladder |
| FIG. 3b | 1 | Buckwheat cake B |
| | | (template DNA amount: 50 ng/tube) |
| | 2 | Buckwheat cake B |
| | | (template DNA amount: 120 ng/tube) |
| | 3 | Buckwheat cake B |
| | | (template DNA amount: 1,800 ng/tube) |
| | 4 | Buckwheat seeds |
| | 5 | Water |
| | M | 100 bp ladder |

FAG 19/22 were used in the processed foods for the detection of buckwheat (Experiment 3). As a result, except the buckwheat cake B, the buckwheat was detected in the defined template DNA amount of 25 ng per PCR (FIG. 3a). On the other hand, in the buckwheat cake B, even when the template DNA was further added to increase the amount to 50 ng or 120 ng, no PCR amplified band was observed, but when the template DNA amount was increased to 1,800 ng, the detection of buckwheat became possible (FIG. 3b).

Food allergy tests currently carried out in the clinical settings include provocative test, skin prick test and RAST method. However, the targets in the tests by these methods are patients suffering from allergies or blood thereof and it is difficult to apply these methods to food analysis. On the other hand, electrophoresis (SDS-PAGE), western blotting, and immunochemical methods (ELISA) have been used for isolating and detecting a specific protein for the purpose of detecting and quantifying an allergen per se and these methods are effective for the detection of known major allergens. However, these methods are not necessarily appropriate for the detection of unknown allergens or in processed foods in which proteins may be potentially denatured by heating.

INDUSTRIAL APPLICABILITY

DNAs very often remain in processed foods because of their higher heating resistance than proteins. Therefore, the method for detecting a specified substance based on a PCR method according to the present invention is significantly useful particularly in processed foods as a means for indirectly analyzing a substance causative of an allergy in a food, which compensates for conventional protein detection methods.

The invention claimed is:

1. A method for detecting the presence/absence of buckwheat in a product, comprising the steps of:
performing PCR on a sample from said product with the primer pair FAG 19 (SEQ ID NO:7)/FAG 22(SEQ ID NO:9);
and evaluating the results of said PCR step to determine whether buckwheat is present or absent in said product.

2. The method according to claim 1, wherein a clear amplified band is observed in analytes including tatary buckwheat (Fagopyrum tataricum) and/or buckwheat (Fagopyrum esculentum) but is not observed in analytes including wild buckwheat (Fallopia) on an electrophoretic pattern after PCR is performed using the primers.

3. The method according to claim 1, wherein the detection limit of said PCR is 50 ppm.

4. A method of measuring the presence/absence of buckwheat in a food product comprising:
obtaining DNA present in the food, performing PCR of the DNA with the primer pair FAG 19(SEQ ID NO:7)/FAG 22(SEQ ID NO:9), and analyzing the PCR amplification to determine the absence of buckwheat in the food product.

5. The method according to claim 4, wherein the food comprises a processed food.

6. The method according to claim 4, wherein the food comprises a food raw material.

7. The method according to claim 4, wherein a clear amplified band is observed in analytes including tatary buckwheat (Fagopyrum tataricum) and/or buckwheat (Fagopyrum esculentum) but is not observed in analytes including wild buckwheat (Fallopia) on an electrophoretic pattern after PCR is performed using the primers.

8. The method according to claim 4, wherein the detection limit of said PCR is 50 ppm.

9. A method of measuring the presence/absence of buckwheat in a food product comprising;
obtaining DNA present in the food,
performing PCR of the DNA with the primer pairs FAG 19 (SEQ ID NO:7)/FAG 22(SEQ ID NO:9),
analyzing the PCR amplification,
obtaining information as to whether the food contains buckwheat with food allergy or suspect thereof, and indicating the information about the food.

* * * * *